US008232248B2

(12) United States Patent
Kjaer et al.

(10) Patent No.: US 8,232,248 B2
(45) Date of Patent: Jul. 31, 2012

(54) TREATMENT OF RHEUMATOID ARTHRITIS WITH MAMMAL BETA DEFENSINS

(75) Inventors: Tanja Maria Rosenkilde Kjaer, Holte (DK); Thomas Kruse, Copenhagen N (DK); Per Holse Mygind, Vaerloese (DK); Karoline Sidelmann Brinch, Copenhagen NV (DK); Soeren Kjaerulff, Holte (DK); Birgitte Andersen, Bagsvaerd (DK)

(73) Assignee: Novozymes Adenium Biotech A/S, Bagsvaerd (DK)

( * ) Notice: Subject to any disclaimer, the term of this patent is extended or adjusted under 35 U.S.C. 154(b) by 142 days.

(21) Appl. No.: 12/504,920

(22) Filed: Jul. 17, 2009

(65) Prior Publication Data

US 2010/0016231 A1  Jan. 21, 2010

Related U.S. Application Data

(60) Provisional application No. 61/086,910, filed on Aug. 7, 2008, provisional application No. 61/179,517, filed on May 19, 2009.

(30) Foreign Application Priority Data

Jul. 18, 2008 (EP) .................................... 08160761
May 15, 2009 (EP) .................................... 09160448

(51) Int. Cl.
*A61K 38/00* (2006.01)
*A61P 31/00* (2006.01)
*A61P 31/04* (2006.01)

(52) U.S. Cl. .......................... 514/16.6; 514/1.1; 514/2.3

(58) Field of Classification Search .................... None
See application file for complete search history.

(56) References Cited

U.S. PATENT DOCUMENTS

| | | | | |
|---|---|---|---|---|
| 2006/0115480 A1* | 6/2006 | Hillman | .................... | 424/146.1 |
| 2008/0194481 A1 | 8/2008 | Rosen et al. | | |
| 2010/0016230 A1 | 1/2010 | Kjaer et al. | | |
| 2010/0016232 A1 | 1/2010 | Kjaer et al. | | |

FOREIGN PATENT DOCUMENTS

| | | |
|---|---|---|
| WO | WO 2007/007116 A1 | 1/2007 |
| WO | WO 2007/081486 | 7/2007 |
| WO | WO 2007/087557 A2 | 8/2007 |
| WO | WO 2009/033776 A1 | 3/2009 |

OTHER PUBLICATIONS

Kawada et al., 2007, World Journal of Gastroenterology, vol. 13, No. 42, pp. 5581-5593.
Pazgier et al., 2006, Cellular and Molecular Life Sciences, vol. 63, pp. 1294-1313.
Rubbert-Roth et al., 2009, Arthritis Research and Therapy, vol. 11, pp. 1-12.
Wehkamp et al., 2002, European Journal of Gastroenterology & Hepatology, vol. 14, No. 7, pp. 745-752.
Wehkamp et al., 2003, Inflammatory Bowel Diseases, vol. 9, No. 4, pp. 215-223.
Wehkamp et al., 2005, Journal of Leukocyte Biology, vol. 77, pp. 460-465.
Wirtz et al., 2007, Advanced Drug Delivery Reviews vol. 59, pp. 1073-1083.
Boniotto et al., Antimicrobiol Agents and Chemotheraphy, vol. 50, No. 4, pp. 1433-1441 (2006).
Bowdish et al., CTMI, vol. 306, pp. 27-66 (2006).
Gersemann et al., World Journal of Gastroentology, vol. 14, No. 36, pp. 5499-5503 (2008).
Lehrer, Nature Reviews Microbiology, vol. 2, pp. 727-738 (2004).
Niyonsaba et al., Journal of Investigative Dermatology, vol. 127, pp. 594-604 (2007).
Otte et al., Journal of Cellular Biochemistry, vol. 104, pp. 2286-2297 (2008).
Rowland et al., Immunopharmacology, vol. 40, pp. 11-20 (1998).
Schneider et al., J. Mol. Med., vol. 83, pp. 587-595 (2005).
Swidsinski et al., Gastroenterology, vol. 122, pp. 44-54 (2002).
Wehkamp et al., PNAS, vol. 102, (50), pp. 18129-18134 (2005).
Wang et al., Expert Rev. Anti. Infect. Ther., vol. 5, No. 6, pp. 1049-1057 (2007).
Aldhous, M.C., et al., "Dysregulation of Human β-defensin-2 Protein in Inflammatory Bowel Disease," *PLoS One* 4(7, article e6285) (2009).
Asadullah, K., et al., "IL-10 Is a Key Cytokine in Psoriasis. Proof of Principle by IL-10 Therapy: A New Therapeutic Approach," *J. Clin. Invest.* 101(4):783-794 (1998).
Berg, D.J., et al., "Enterocolitis and Colon Cancer in Interleukin-10-deficient Mice are Associated With Aberrant Cytokine Production and CD4+3 Th1-like Responses," *J Clin Invest*, 98:1010-20. (1996).
Bhavsar, M.D., and Amiji, M.M., "Oral IL-10 gene delivery in a microsphere-based formulation for local transfection and therapeutic efficacy in inflammatory bowel disease," *Gene Ther.* 15:1200-1209 (2008).
Chronnell, C.M.T., et. al., "Human β Defensin-1 and -2 Expression in Human Pilosebaceous Units: Upregulation in *Acne vulgaris* Lesions," *J Invest. Dermatol.*, 117:1120-1125 (2001).
de Jongh, G.J., et. al., "High expression levels of keratinocyte anti-microbial proteins in psoriasis compared with atopic dermatitis," *J. Invest. Dermatol.*, 125: 1163-1173 (2005).
Duvallet E., et al., "A key cytokine in inflammatory diseases," *Annals of Medicine*, 43:503-511 (2011).
Fahlgren, A., et al., "Increased expression of antimicrobial peptides and lysozyme in colonic epithelial cells of patients with ulcerative colitis," *Clin Exp Immunol* 131:90-101 (2003).
Fedorak, R.N., et al., "Recombinant Human Interleukin 10 in the Treatment of Patients With Mild to Moderately Active Crohn's Disease," *Gastroenterology* 119:1473-1482 (2000).
Feldmann M., and Maini R.N., "TNF defined as a therapeutic target for rheumatoid arthritis and other autoimmune diseases," *Nat. Med.* 9(10):1245-1250. (2003).
Fellowes, R., et al., "Amelioration of established collagen induced arthritis by systemic IL-10 gene delivery," *Gene Ther.* 7: 967-977 (2000).

(Continued)

Primary Examiner — Daniel C Gamett
(74) *Attorney, Agent, or Firm* — Hamilton, Brook, Smith & Reynolds, PC

(57) ABSTRACT

The present invention relates to treatment of rheumatoid arthritis with mammal beta defensins.

9 Claims, No Drawings

OTHER PUBLICATIONS

Finnegan, A., et al., "Collagen-induced arthritis is exacerbated in IL-10-deficient mice," *Arthritis Res. Ther.* 5(1): R18-R24 (2003).

Finnegan, A., et al., "Proteoglycan (aggrecan)-induced arthritis in BALB/c mice is a Th1-type disease regulated by Th2 cytokines," *J. Immunol.* 163: 5383-5390 (1999).

Gambichler, T., et al., "Expression of human β-defensins in patients with mycosis fungoides," *Arch Dermatol Res* 299: 221-224 (2007).

Jansen, P.A.M., et al., β-Defensin-2 Protein Is a Serum Biomarker for Disease Activity in Psoriasis and Reaches Biologically Relevant Concentrations in Lesional Skin, *PLoS One* 4(3): e4725-e4725 (2009).

Kapel, N., et al., "Fecal β-Defensin-2 in Children With Inflammatory Bowel Diseases," *Journal of Pediatric Gastroenterology & Nutrition* 48:117-120 (2008).

Kasama, T., et al., "Interleukin-10 expression and chemokine regulation during the evolution of murine type II collagen-induced arthritis," *J. Clin. Invest.* 95: 2868-2876 (1995).

Lindsay J.O., et al., "Local delivery of adenoviral vectors encoding murine interleukin 10 induces colonic interleukin 10 production and is therapeutic for murine colitis," *Gut* 52:363-369 (2003).

Maini, R.N., et al. "rHUIL-10 in subjects with active rheumatoid arthritis (RA): A phase I and cytokine response study," *Arthritis Rheum.* 40:Abstract 1161, p. S224 (1997).

Mirandola S.R., et al.. "Interferon-beta modifies the peripheral blood cell cytokine secretion in patients with multiple sclerosis," *Int Immunopharmacol* 9: 824-830 (2009).

Nakase H., et al., "New cytokine delivery system using gelatin microspheres containing interleukin-10 for experimental inflammatory bowel disease," *J Pharmacol Exp Ther* 301(1):59-65, (2002).

Özenci V, et al., "Multiple sclerosis is associated with an imbalance between tumour necrosis factor-alpha (TNF-α)- and IL-10-secreting blood cells that is corrected by interferon-beta (IFN-β) treatment," *Clin Exp Immunol* 120:147-153 (2000).

Schreiber, S., et al., "Safety and Efficacy of Recombinant Human Interleukin 10 in Chronic Active Crohn's Disease," *Gastroenterology* 119:1461-1472 (2000).

Singh, P.K., et al., "Production of β-defensins by human airway epithelia," *Proc. Natl. Acad. Sci. USA* 95:14961-14966 (1998).

Smeets, T.J.M., et al., "Analysis of serial synovial biopsies in patients with rheumatoid arthritis: description of a control group without clinical improvement after treatment with interleukin 10 or placebo," *J Rheumatol.* 26(10):2089-2093 (1999).

Steidler, L., et al., "Treatment of murine colitis by *Lactococcus lactis* secreting interleukin-10," *Science* 289:1352-1355 (2000).

van Roon, J.A.G., et al., "Interleukin 10 treatment of patients with rheumatoid arthritis enhances Fcγ receptor expression on monocytes and responsiveness to immune complex stimulation," *J Rheumatol.* 30(4):648-651 (2003).

Vordenbaumen, S., et al., "Elevated levels of human beta-defensin 2 and human neutrophil peptides in systemic lupus erythematosus," *Lupus* 19:1648-1653 (2010).

Walmsley M., et al., "Interleukin-10 inhibition of the progression of established collagen-induced arthritis," *Arthritis Rheum* 39(3):495-503 (1996).

Yudoh, K., et al., "Reduced expression of the regulatory CD4+ T cell subset is related to Th1/Th2 balance and disease severity in rheumatoid arthritis," *Arthritis Rheum* 43(3): 617-627 (2000).

Zhang, X., et al., "IL-10 is involved in the suppression of experimental autoimmune encephalomyelitis by $CD25^+CD4^+$ regulatory T cells," *Int Immunol* 16(2):249-256 (2003).

Office Action, U.S. Appl. No. 12/504,909, mailed Mar. 28, 2011.
Reply, U.S. Appl. No. 12/504,909, filed Jun. 28, 2011.
Final Office Action, U.S. Appl. No. 12/504,909, mailed Aug. 25, 2011.
Reply, U.S. Appl. No. 12/504,909, filed Dec. 22, 2011.
Office Action, U.S. Appl. No. 12/504,930, mailed Aug. 25, 2011.
Reply, U.S. Appl. No. 12/504,930, filed Dec. 22, 2011.

\* cited by examiner

SEQUENCE LISTING

```
<160> NUMBER OF SEQ ID NOS: 6

<210> SEQ ID NO 1
<211> LENGTH: 36
<212> TYPE: PRT
<213> ORGANISM: Homo sapiens
<220> FEATURE:
<221> NAME/KEY: mat_peptide
<222> LOCATION: (1)..(36)

<400> SEQUENCE: 1

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
                20                  25                  30

Lys Cys Cys Lys
        35

<210> SEQ ID NO 2
<211> LENGTH: 41
<212> TYPE: PRT
<213> ORGANISM: Homo sapiens
<220> FEATURE:
<221> NAME/KEY: mat_peptide
<222> LOCATION: (1)..(41)

<400> SEQUENCE: 2

Gly Ile Gly Asp Pro Val Thr Cys Leu Lys Ser Gly Ala Ile Cys His
1               5                   10                  15

Pro Val Phe Cys Pro Arg Arg Tyr Lys Gln Ile Gly Thr Cys Gly Leu
                20                  25                  30

Pro Gly Thr Lys Cys Cys Lys Lys Pro
        35                  40

<210> SEQ ID NO 3
<211> LENGTH: 45
```

```
<212> TYPE: PRT
<213> ORGANISM: Homo sapiens
<220> FEATURE:
<221> NAME/KEY: mat_peptide
<222> LOCATION: (1)..(45)

<400> SEQUENCE: 3

Gly Ile Ile Asn Thr Leu Gln Lys Tyr Tyr Cys Arg Val Arg Gly Gly
1               5                   10                  15

Arg Cys Ala Val Leu Ser Cys Leu Pro Lys Glu Glu Gln Thr Gly Lys
            20                  25                  30

Cys Ser Thr Arg Gly Arg Lys Cys Cys Arg Arg Lys Lys
        35                  40                  45

<210> SEQ ID NO 4
<211> LENGTH: 50
<212> TYPE: PRT
<213> ORGANISM: Homo sapiens
<220> FEATURE:
<221> NAME/KEY: mat_peptide
<222> LOCATION: (1)..(50)

<400> SEQUENCE: 4

Glu Phe Glu Leu Asp Arg Ile Cys Gly Tyr Gly Thr Ala Arg Cys Arg
1               5                   10                  15

Lys Lys Cys Arg Ser Gln Glu Tyr Arg Ile Gly Arg Cys Pro Asn Thr
            20                  25                  30

Tyr Ala Cys Cys Leu Arg Lys Trp Asp Glu Ser Leu Leu Asn Arg Thr
        35                  40                  45

Lys Pro
    50

<210> SEQ ID NO 5
<211> LENGTH: 37
<212> TYPE: PRT
<213> ORGANISM: Artificial Sequence
<220> FEATURE:
<223> OTHER INFORMATION: hBD-4 variant consisting of amino acids 3-39
      of SEQ ID NO:4
<220> FEATURE:
<221> NAME/KEY: mat_peptide
<222> LOCATION: (1)..(37)

<400> SEQUENCE: 5

Glu Leu Asp Arg Ile Cys Gly Tyr Gly Thr Ala Arg Cys Arg Lys Lys
1               5                   10                  15

Cys Arg Ser Gln Glu Tyr Arg Ile Gly Arg Cys Pro Asn Thr Tyr Ala
            20                  25                  30

Cys Cys Leu Arg Lys
        35

<210> SEQ ID NO 6
<211> LENGTH: 40
<212> TYPE: PRT
<213> ORGANISM: Mus musculus
<220> FEATURE:
<221> NAME/KEY: mat_peptide
<222> LOCATION: (1)..(40)

<400> SEQUENCE: 6

Lys Ile Asn Asn Pro Val Ser Cys Leu Arg Lys Gly Gly Arg Cys Trp
1               5                   10                  15
```

```
Asn Arg Cys Ile Gly Asn Thr Arg Gln Ile Gly Ser Cys Gly Val Pro
            20                  25                  30

Phe Leu Lys Cys Cys Lys Arg Lys
            35          40
```

TREATMENT OF RHEUMATOID ARTHRITIS WITH MAMMAL BETA DEFENSINS

CROSS-REFERENCE TO RELATED APPLICATIONS

This application claims priority or the benefit under 35 U.S.C. 119 of European application nos. EP08160761.6 filed Jul. 18, 2008, and EP09160448.8 filed May 15, 2009, and U.S. provisional application Nos. 61/086,910 filed Aug. 7, 2008, and 61/179,517 filed May 19, 2009, the contents of which are fully incorporated herein by reference.

REFERENCE TO A SEQUENCE LISTING

This application contains a Sequence Listing in computer readable form. The computer readable form is incorporated herein by reference.

BACKGROUND OF THE INVENTION

1. Field of the Invention

The present invention relates to prevention and treatment of rheumatoid arthritis by administration of a human beta defensin.

2. Background

Among many other elements, key components of innate immunity are the antimicrobial peptides (AMPs) that individually show considerable selectivity, but collectively are able to rapidly kill a broad spectrum of bacteria, viruses and fungi. The biological significance of AMPs is emphasized by their ubiquitous distribution in nature and they are probably produced by all multicellular organisms. In humans the predominant AMPs are the defensins. The human defensins are small cationic peptides that can be divided into α- and β-defensins based on the topology of their three intramolecular cysteine disulphide bonds. The α-defensins can be further subdivided into those that were first isolated from neutrophil granules (HNP1-4) and those that are expressed by Paneth cells in the crypts of the small intestine (HD5 and HD6). The β-defensins are mainly produced by epithelial cells in various tissues and organs including the skin, trachea, gastrointestinal tract, urogenital system, kidneys, pancreas and mammary gland. The best characterized members of the β-defensin family are hBD1-3. However, using various bioinformatics tools almost 40 open reading frames encoding putative β-defensin homologues have been annotated in the human genome. Some of the human defensins are produced constitutively, whereas others are induced by proinflammatory cytokines or exogenous microbial products.

It has become increasingly clear that the human defensins in addition to their direct antimicrobial activity also have a wide range of immunomodulatory/alternative properties. These include the induction of various chemokines and cytokines, chemotactic and apoptotic activities, induction of prostaglandin, histamine and leukotriene release, inhibition of complement, stimulation of dendritic cell maturation through toll-like receptor signaling and stimulation of pathogen clearance by neutrophils. Furthermore, the human defensins also play a role in wound healing, proliferation of epithelial and fibroblast cells, angiogenesis and vasculogenesis.

There is increasing evidence that the human defensins play an important role in many infectious and inflammatory diseases. Overexpression of human defensins is often observed in inflamed and/or infected skin most likely because of local induction by microbial components or endogenous proinflammatory cytokines. In psoriasis hBD2 and hBD3 are overabundant and in lesional epithelium of patients with acne vulgaris or superficial folliculitis a significant upregulation of hBD2 has been observed. On the other hand, downregulation of hBD2 and hBD3 has been associated with atopic dermatitis.

Rheumatoid arthritis is a chronic, systemic inflammatory disorder that may affect many tissues and organs, but principally attacks the joints producing a inflammatory synovitis that often progresses to destruction of the articular cartilage and ankylosis of the joints. Rheumatoid arthritis can also produce diffuse inflammation in the lungs, pericardium, pleura, and sclera, and also nodular lesions, most common in subcutaneous tissue under the skin. Although the cause of rheumatoid arthritis is unknown, autoimmunity plays a pivotal role in its chronicity and progression.

DETAILED DESCRIPTION OF THE INVENTION

Definitions

Defensin: The term "defensin" as used herein refers to polypeptides recognized by a person skilled in the art as belonging to the defensin class of antimicrobial peptides. To determine if a polypeptide is a defensin according to the invention, the amino acid sequence may be compared with the hidden markov model profiles (HMM profiles) of the PFAM database by using the freely available HMMER software package.

The PFAM defensin families include for example Defensin_1 or "Mammalian defensin" (accession no. PF00323), and Defensin_2 or Defensin_beta or "Beta Defensin" (accession no. PF00711).

The defensins of the invention belong to the beta defensin class. The defensins from the beta defensin class share common structural features, such as the cysteine pattern.

Examples of defensins, according to the invention, include human beta defensin 1 (hBD1; see SEQ ID NO:1), human beta defensin 2 (hBD2; see SEQ ID NO:2), human beta defensin 3 (hBD3; see SEQ ID NO:3), human beta defensin 4 (hBD4; see SEQ ID NO:4), and mouse beta defensin 3 (mBD3; see SEQ ID NO:6).

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277; http://emboss.org), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

$$(\text{Identical Residues} \times 100)/(\text{Length of Alignment} - \text{Total Number of Gaps in Alignment})$$

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra; http://emboss.org), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the —nobrief option) is used as the percent identity and is calculated as follows:

(Identical Deoxyribonucleotides×100)/(Length of Alignment−Total Number of Gaps in Alignment).

Isolated polypeptide: The term "isolated variant" or "isolated polypeptide" as used herein refers to a variant or a polypeptide that is isolated from a source. In one aspect, the variant or polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form. This can be accomplished, for example, by preparing the polypeptide by well-known recombinant methods or by classical purification methods.

Mammal Beta Defensins

The present invention relates to pharmaceutical uses of mammal beta defensins, such as human beta defensins and/or mouse beta defensins, in the treatment of rheumatoid arthritis. The treatment is preferably associated with reduced TNF-alpha activity in treated tissues.

In an embodiment, the mammal beta defensins of the invention have a degree of identity of at least 80%, preferably at least 85%, more preferably at least 90%, and most preferably at least 95% to any of the amino acid sequences of SEQ ID NO:1, SEQ ID NO:2, SEQ ID NO:3, SEQ ID NO:4, SEQ ID NO:5 and/or SEQ ID NO:6. In a preferred embodiment, the mammal beta defensins of the invention have a degree of identity of at least 80%, preferably at least 85%, more preferably at least 90%, and most preferably at least 95% to any of the amino acid sequences of SEQ ID NO:1, SEQ ID NO:2, SEQ ID NO:3 and/or SEQ ID NO:4. In a more preferred embodiment, the mammal beta defensins of the invention consist of human beta defensin 1 (SEQ ID NO:1), human beta defensin 2 (SEQ ID NO:2), human beta defensin 3 (SEQ ID NO:3), human beta defensin 4 (SEQ ID NO:4), a variant of human beta defensin 4 (SEQ ID NO:5) and/or mouse beta defensin 3 (SEQ ID NO:6). In an even more preferred embodiment, the mammal beta defensins of the invention consist of human beta defensin 1 (SEQ ID NO:1), human beta defensin 2 (SEQ ID NO:2), human beta defensin 3 (SEQ ID NO:3) and/or human beta defensin 4 (SEQ ID NO:4).

In another embodiment, the mammal beta defensins of the invention have a degree of identity of at least 80%, preferably at least 85%, more preferably at least 90%, and most preferably at least 95% to the amino acid sequence of SEQ ID NO:2. In a preferred embodiment, the mammal beta defensins of the invention consist of human beta defensin 2 (SEQ ID NO:2).

In yet another embodiment, the mammal beta defensins of the invention consist of human beta defensins and/or mouse beta defensins, and functionally equivalent variants thereof. Preferably, the mammal beta defensins consist of human beta defensin 1, human beta defensin 2, human beta defensin 3, human beta defensin 4 and mouse beta defensin 3, and functionally equivalent variants thereof. More preferably, the mammal beta defensins of the invention consist of human beta defensin 2, and functionally equivalent variants thereof.

The mammal beta defensins of the invention are also referred to as compounds of the preferred embodiments.

In the context of the present invention, a "functionally equivalent variant" of a mammal (e.g. human) beta defensin is a modified mammal (e.g. human) beta defensin exhibiting approx. the same effect on rheumatoid arthritis as the parent mammal (e.g. human) beta defensin. Preferably, it also exhibits approx. the same effect on TNF-alpha activity as the mammal (e.g. human) beta defensin.

According to the invention, a functionally equivalent variant of a mammal (e.g. human) beta defensin may comprise 1-5 amino acid modifications, preferably 1-4 amino acid modifications, more preferably 1-3 amino acid modifications, most preferably 1-2 amino acid modification(s), and in particular one amino acid modification, as compared to the mammal (e.g. human) beta defensin amino acid sequence.

The term "modification" means herein any chemical modification of a mammal (e.g. human) beta defensin. The modification(s) can be substitution(s), deletion(s) and/or insertions(s) of the amino acid(s) as well as replacement(s) of amino acid side chain(s); or use of unnatural amino acids with similar characteristics in the amino acid sequence. In particular the modification(s) can be amidations, such as amidation of the C-terminus.

Preferably, amino acid modifications are of a minor nature, that is conservative amino acid substitutions or insertions that do not significantly affect the folding and/or activity of the polypeptide; single deletions; small amino- or carboxyl-terminal extensions; a small linker peptide of up to about 20-25 residues; or a small extension that facilitates purification by changing net charge or another function, such as a polyhistidine tag, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Essential amino acids in the mammal beta defensins can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., activity against rheumatoid arthritis) to identify amino acid residues that are critical to the activity of the molecule. See also, Hilton et al., 1996, *J. Biol. Chem.* 271: 4699-4708. The identities of essential amino acids can also be inferred from analysis of identities with polypeptides which are related to mammal (e.g. human) beta defensins.

Single or multiple amino acid substitutions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30:10832-10837; U.S. Pat. No. 5,223,409; WO 92/06204), and region-directed mutagenesis (Derbyshire et al., 1986, *Gene* 46:145; Ner et al., 1988, *DNA* 7:127).

An N-terminal extension of the polypeptides of the invention may suitably consist of from 1 to 50 amino acids, preferably 2-20 amino acids, especially 3-15 amino acids. In one embodiment N-terminal peptide extension does not contain an Arg (R). In another embodiment the N-terminal extension comprises a kex2 or kex2-like cleavage site as will be defined further below. In a preferred embodiment the N-terminal extension is a peptide, comprising at least two Glu (E) and/or Asp (D) amino acid residues, such as an N-terminal extension comprising one of the following sequences: EAE, EE, DE and DD.

Methods and Uses

Human beta defensin 2 was found to significantly reduce the severity of disease parameters in a 41-Day collagen-induced rheumatoid arthritis model in the mouse; thus showing potent activity as a medicament for treatment of rheumatoid arthritis.

The present invention therefore provides methods of treating rheumatoid arthritis, which treatment comprises administering to a subject in need of such treatment an effective amount of a mammal beta defensin, preferably a human beta defensin, more preferably human beta defensin 2, e.g., in the form of a pharmaceutical composition. Also provided are mammal beta defensins, preferably human beta defensins, more preferably human beta defensin 2, for the manufacture of a medicament, and the use of mammal beta defensins, preferably human beta defensins, more preferably human beta defensin 2, for the manufacture of a medicament for the treatment of rheumatoid arthritis. Treatment includes treatment of an existing disease or disorder, as well as prophylaxis (prevention) of a disease or disorder.

Mammal beta defensins can be employed therapeutically in compositions formulated for administration by any conventional route, including enterally (e.g., buccal, oral, nasal, rectal), parenterally (e.g., intravenous, intracranial, intraperitoneal, subcutaneous, or intramuscular), or topically (e.g., epicutaneous, intranasal, or intratracheal). Within other embodiments, the compositions described herein may be administered as part of a sustained release implant.

Within yet other embodiments, compositions, of preferred embodiments may be formulized as a lyophilizate, utilizing appropriate excipients that provide stability as a lyophilizate, and subsequent to rehydration.

Pharmaceutical compositions containing a mammal beta defensin can be manufactured according to conventional methods, e.g., by mixing, granulating, coating, dissolving or lyophilizing processes.

Pharmaceutical compositions of preferred embodiments comprise a mammal beta defensin and a pharmaceutically acceptable carrier and/or diluent.

A mammal beta defensin is preferably employed in pharmaceutical compositions in an amount which is effective to treat rheumatoid arthritis, preferably with acceptable toxicity to the patient. For such treatment, the appropriate dosage will, of course, vary depending upon, for example, the chemical nature and the pharmacokinetic data of a compound of the present invention used, the individual host, the mode of administration and the nature and severity of the conditions being treated. However, in general, for satisfactory results in larger mammals, for example humans, an indicated daily dosage is preferably from about 0.001 mg/kg body weight to about 100 mg/kg body weight, preferably from about 0.01 mg/kg body weight to about 50 mg/kg body weight, more preferably from about 0.05 mg/kg body weight to about 20 mg/kg body weight, and most preferably from about 0.1 mg/kg body weight to about 10 mg/kg body weight, for example, administered in divided doses up to one, two, three, or four times a day. The compounds of preferred embodiments can be administered to larger mammals, for example humans, by similar modes of administration at similar dosages than conventionally used.

In certain embodiments, the pharmaceutical compositions of preferred embodiments can include mammal beta defensins, such as human beta defensins, in an amount of about 0.5 mg or less to about 1500 mg or more per unit dosage form depending upon the route of administration, preferably from about 0.5, 0.6, 0.7, 0.8, or 0.9 mg to about 150, 200, 250, 300, 350, 400, 450, 500, 600, 700, 800, 900, or 1000 mg, and more preferably from about 1, 2, 3, 4, 5, 6, 7, 8, 9, 10, 15, 20, or 25 mg to about 30, 35, 40, 45, 50, 55, 60, 65, 70, 75, 80, 85, 90, 95, or 100 mg. In certain embodiments, however, lower or higher dosages than those mentioned above may be preferred. Appropriate concentrations and dosages can be readily determined by one skilled in the art.

Pharmaceutically acceptable carriers and/or diluents are familiar to those skilled in the art. For compositions formulated as liquid solutions, acceptable carriers and/or diluents include saline and sterile water, and may optionally include antioxidants, buffers, bacteriostats, and other common additives. The compositions can also be formulated as pills, capsules, granules, tablets (coated or uncoated), (injectable) solutions, solid solutions, suspensions, dispersions, solid dispersions (e.g., in the form of ampoules, vials, creams, gels, pastes, inhaler powder, foams, tinctures, lipsticks, drops, sprays, or suppositories). The formulation can contain (in addition to a mammal beta defensin, and other optional active ingredients) carriers, fillers, disintegrators, flow conditioners, sugars and sweeteners, fragrances, preservatives, stabilizers, wetting agents, emulsifiers, solubilizers, salts for regulating osmotic pressure, buffers, diluents, dispersing and surface-active agents, binders, lubricants, and/or other pharmaceutical excipients as are known in the art. One skilled in this art may further formulate a mammal beta defensin in an appropriate manner, and in accordance with accepted practices, such as those described in Remington's Pharmaceutical Sciences, Gennaro, Ed., Mack Publishing Co., Easton, Pa. 1990.

A mammal beta defensin can be used alone, or in combination therapies with one, two, or more other pharmaceutical compounds or drug substances, and/or with one or more pharmaceutically acceptable excipient(s).

In vitro Synthesis

Mammal beta defensins may be prepared by in vitro synthesis, using conventional methods as known in the art. Various commercial synthetic apparatuses are available, for example automated synthesizers by Applied Biosystems Inc., Beckman, etc. By using synthesizers, naturally occurring amino acids may be substituted with unnatural amino acids, particularly D-isomers (or D-forms) e.g. D-alanine and D-isoleucine, diastereoisomers, side chains having different lengths or functionalities, and the like. The particular sequence and the manner of preparation will be determined by convenience, economics, purity required, and the like.

Chemical linking may be provided to various peptides or proteins comprising convenient functionalities for bonding, such as amino groups for amide or substituted amine formation, e.g. reductive amination, thiol groups for thioether or disulfide formation, carboxyl groups for amide formation, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

Mammal beta defensins may also be isolated and purified in accordance with conventional methods of recombinant synthesis. A lysate may be prepared of the expression host and the lysate purified using HPLC, exclusion chromatography, gel electrophoresis, affinity chromatography, or other purification technique.

The present invention is further described by the following examples that should not be construed as limiting the scope of the invention.

EXAMPLES

Example 1

Evaluation of Human Beta Defensin 2 in a Collagen-Induced Rheumatoid Arthritis Model During testing of hBD2 for immunomodulatory effects it was unexpectedly observed that hBD2 had vast anti-inflammatory potential.

Here, we have shown that hBD2 has significant effect in treating rheumatoid arthritis in a collagen-induced rheumatoid arthritis model in the mouse.

Human Beta Defensin 2 (hBD2)

hBD2 was produced recombinantly. A synthetic DNA fragment (DNA 2.0) encoding hBD2 was cloned into the pET-32(+) expression vector (Novagen). The resulting plasmid encoded a translational fusion peptide containing an N-terminal thioredoxin part followed by a his-tag, an enterokinase cleavage site and finally the hBD2 peptide. The expression plasmid was transformed into $E.\ coli$ strain BL21.

An overnight culture of this strain was diluted 100 fold in TB-glycerol containing 100 μg/ml of ampicillin and grown to an OD600 of approximately 8 at 37° C. and induced with 0.5 mM of IPTG for 3 hours after which the cells were harvested by centrifugation. The his-tagged trx-hBD2 fusion peptide was purified on Ni-NTA beads (QIAGEN) using standard protocols. The his-tag purified fusion peptide was subsequently dialysed over-night into enterokinase buffer (50 mM tris-HCl pH 7.5, 1 mM $CaCl_2$) and cleaved with enterokinase to release mature hBD2. The hBD2 peptide was further purified by cation-exchange chromatography using Source 15 S matrix (Amersham Biosciences). The correct molecular weight of hBD2 was verified using MALDI-TOF mass spectrometry.

Production of mBD3 (see Example 5) was carried out using an identical protocol.

The proper folding and disulphide-bridge topology of the hBD2 molecule was subsequently verified using tryptic digestion coupled with LC-MS and NMR spectroscopy.

Endotoxin was removed by preparative RP-HPLC at low pH, and the content of endotoxin was determined by a LAL assay (Endosafe KTA2) and the level was found to be below the detection limit of the assay (0.05 EU/mg). To ascertain that levels below the detection limit of the endotoxin assay were not able to stimulate PBMC, titration curves of stimulation with a very potent lipopolysaccharide ($E.\ coli$, O111 :B4, Sigma L4391) were performed. Very low levels of this LPS (0.06 pg/ml) were able to stimulate PBMC to a detectable cytokine production.

The aim of the following study was to determine the anti-inflammatory activity of human beta defensin 2 in rheumatoid arthritis.

Test System

Species/Strain: Mouse/DBA/1

Source: Harlan, UK

Gender: Male

No. of Animals: n=50

Age: Young adults, 6-8 weeks of age at study initiation.

Body Weight: Weight variation of study animals at the time of collagen induction did not exceed ±20% of the mean weight.

Animals Health: The health status of the animals used in this study was examined on arrival. Only animals in good health were acclimatized to laboratory conditions and were used in the study.

Acclimatization: At least 7 days.

Housing: During acclimatization and following dosing, animals were housed within a limited access rodent facility and kept in groups of maximum 10 mice, in polypropylene cages (45 cm×25 cm×13 cm), fitted with solid bottoms and filled with wood shavings as bedding material. Cages were changed once weekly.

Food and Water: Animals were provided ad libitum a commercial rodent diet and free access to drinking water, supplied to each cage via polyethylene bottles with stainless steel sipper tubes. Water bottles were changed at least every 3 weeks. Water was changed 3 times per week.

Environment: Automatically controlled environmental conditions were set to maintain temperature at 20-24° C. with a relative humidity (RH) of 30-70%, a 12/12 hour light/dark cycle and 10-30 air changes/hr in the study room. Temperature and RH was monitored daily by both manual measurements and the control computer. The light cycle was monitored by the control computer.

Identification: Animals were given a unique animal identification ear number. This number also appeared on a cage card, visible on the front of each cage. The cage card also contained the study number.

Randomization: Animals were randomly assigned to experimental groups.

Termination: At the end of the study surviving animals were euthanized by $O_2/CO_2$ inhalation, followed by exsanguination.

Justification: The mouse was selected since it represented the species of choice for this experimental animal model. The DBA/1 strain of mouse is highly susceptible to collagen-induced arthritis (CIA).

Materials

Human Beta Defensin 2 (hBD2); see above

Dexamethasone (Sigma, cat. no. D1756)

Bovine Type II Collagen (MD Biosciences, cat. no. 804001314)

Complete Freund's Adjuvant (CFA) (MD Biosciences, cat. no. 501009703)

PBS (PAA, cat no. H15-002)

Constitution of Test Groups

TABLE 1

Test groups and treatments.

| Group size | Group no. | Test compound | Route | Dose | Volume | Regime |
|---|---|---|---|---|---|---|
| n = 10 | A | Vehicle control | IV | 0 mg/kg | 5 mL/kg | once daily |
| n = 10 | B | Dexamethasone | IP | 1 mg/kg | 5 mL/kg | once daily |
| n = 10 | C | hBD2 | IV | 10 mg/kg | 5 mL/kg | once daily |
| n = 10 | D | hBD2 | IV | 1 mg/kg | 5 mL/kg | once daily |
| n = 10 | E | hBD2 | IV | 0.1 mg/kg | 5 mL/kg | once daily |

IV: intravenous
IP: intraperitoneal

Test Procedures

Arthritis Induction

All animals were subjected on Day 0 of the study (study commencement) to an intradermal injection into the tail of 0.1 ml Type II Collagen/CFA emulsion (200 pg collagen per mouse) under light Isoflurane anesthesia, using a plastic syringe. The location of injection was at an approximate caudal distance of about 1 cm from the base of the tail. A collagen challenge (200 μg/mouse) was presented to the animals by IP injection of collagen and PBS on Day 21.

Treatment

Treatments were commenced on day 14 of the study and continued once daily throughout. All surviving mice were terminated on study day 42.

Route of Administration:

(i) hBD2: Intravenous
(ii) Dexamethasone: Intraperitoneal
(iii) Vehicle Control: Intravenous Dose and Volume Dosage (see also Table 1):

(i) hBD2: 10, 1 or 0.1 mg/kg at 5 mL/kg
(ii) Dexamethasone: 1 mg/kg at 5 mL/kg
(iii) Vehicle Control: 0 mg/kg at 5 mL/kg Analgesia: No analgesic was used during the study.

Observations and Examinations

Arthritis Reactions

Mice were examined for signs of arthritogenic responses in peripheral joints on study day 0, 14, 21 and thereafter five times weekly until termination of the study. Arthritis reactions were reported for each paw according to a 0-4 scale in ascending order of severity as shown below:

| Arthritis Score | Grade |
|---|---|
| No reaction, normal: | 0 |
| Mild, but definite redness and swelling of the ankle/wrist or apparent redness and swelling limited to individual digits, regardless of the number of affected digits: | 1 |
| Moderate to severe redness and swelling of the ankle/wrist: | 2 |
| Redness and swelling of the entire paw including digits: | 3 |
| Maximally inflamed limb with involvement of multiple joints: | 4 |

Clinical Signs

On Day 0, 14, 21 and thereafter five times weekly, careful clinical examinations were carried out and recorded. Observations included changes in skin, fur, eyes, mucous membranes, occurrence of secretions and excretions (e.g. diarrhea) and autonomic activity (e.g. lacrimation, salivation, piloerection, pupil size, unusual respiratory pattern). Changes in gait, posture and response to handling, as well as the presence of bizarre behavior, tremors, convulsions, sleep and coma were also noted.

Prior to day 14 mice were monitored daily for any unusual behaviour.

Body Weights

Determination of individual body weights of animals were made shortly before Arthritis induction on Day 0, 14, 21 and thereafter five times weekly until the termination of the study.

Measurement of Experimental Arthritis

The relative change in both hind paw thickness (left and right, just below the foot pad and above the calcaneum) of each animal was measured in mm on study days 0, 14, 21 and thereafter five times per week using a dial caliper (Kroeplin, Munich, Germany).

Study Termination

All mice were terminated on study day 42.

Sample Collection

At study termination, following $O_2/CO_2$ inhalation, terminal blood samples were obtained from all remaining study animals. Serum was prepared from each sample and stored at −20° C. In addition, the left front and rear paws were collected and stored in formalin, and the right front and rear paws were collected and snap frozen for possible joint RNA analysis.

Humane Endpoints

Animals found in a moribund condition and animals showing severe pain and enduring signs of severe distress were humanely euthanized. In addition, animals showing a decrease of body weight larger than 20% from initial body weight determination were humanely euthanized. Mice with a total arthritic score of 12 or higher were also culled for humane reasons. All animals were euthanized by $O_2/CO_2$ inhalation, followed by exsanguination. Paw samples and terminal blood samples were obtained from all study animals.

Statistical Analysis

Evaluation was primarily based on the mean values for arthritis scores and paw thickness measurements. Where appropriate, analysis of the data by appropriate statistical methods was applied to determine significance of treatment effects. ANOVA followed by Tukey post-hoc analysis (Winstat 2005.1 for Excel) was used to assess statistical differences between treatment groups.

In accordance with Home Office regulations mice with a total clinical score of equal to or greater than 12 were culled due to arthritis severity. The clinical score of these mice at termination was carried forward in the analysis for the remainder of the study in order that the data was not artificially skewed by the removal of high scoring mice.

Animal Care and use Statement

This study was performed according to the UK Home Office regulations for use of animals in scientific procedures.

Animal Care and use Statement

This study was performed according to the UK Home Office regulations for use of animals in scientific procedures.

Results

TABLE 2

Mean clinical arthritis scores determined during the 42 day observation period in the collagen induced male DBA/1 arthritic mice.

| Study Day | Data | Group A Vehicle | Group B Dexamethasone 1 mg/kg | Group C hBD2 10 mg/kg | Group D hBD2 1 mg/kg | Group E hBD2 0.1 mg/kg |
|---|---|---|---|---|---|---|
| 0 | Mean Arthritic Score | 0.0 | 0.0 | 0.0 | 0.0 | 0.0 |
|   | SEM | 0.0 | 0.0 | 0.0 | 0.0 | 0.0 |
| 14 | Mean Arthritic Score | 0.1 | 0.4 | 1.7 | 0.6 | 1.2 |
|   | SEM | 0.1 | 0.2 | 0.6 | 0.3 | 0.5 |
| 21 | Mean Arthritic Score | 3.2 | 0.0 | 3.1 | 2.1 | 3.2 |
|   | SEM | 1.2 | 0.0 | 1.1 | 0.8 | 1.3 |
| 22 | Mean Arthritic Score | 3.4 | 0.0 | 4.3 | 2.3 | 3.6 |
|   | SEM | 1.1 | 0.0 | 1.1 | 0.8 | 1.4 |
| 23 | Mean Arthritic Score | 3.4 | 0.0 | 3.3 | 2.0 | 3.2 |
|   | SEM | 1.1 | 0.0 | 1.2 | 0.7 | 1.3 |
| 26 | Mean Arthritic Score | 4.4 | 0.0* | 4.1 | 2.0 | 3.7 |
|   | SEM | 1.1 | 0.0 | 1.2 | 0.7 | 1.3 |
| 27 | Mean Arthritic Score | 4.8 | 0.0* | 4.1 | 2.0 | 4.1 |
|   | SEM | 1.2 | 0.0 | 1.3 | 0.7 | 1.3 |
| 28 | Mean Arthritic Score | 5.3 | 0.0* | 4.1 | 2.3 | 4.4 |
|   | SEM | 1.1 | 0.0 | 1.2 | 0.8 | 1.3 |
| 29 | Mean Arthritic Score | 6.3 | 0.0* | 4.4 | 2.4 | 5.0 |
|   | SEM | 1.1 | 0.0 | 1.3 | 0.8 | 1.3 |
| 30 | Mean Arthritic Score | 6.8 | 0.0* | 4.9 | 2.7 | 5.9 |
|   | SEM | 1.1 | 0.0 | 1.3 | 0.9 | 1.5 |
| 33 | Mean Arthritic Score | 7.4 | 0.0* | 4.8 | 4.0 | 7.3 |
|   | SEM | 1.1 | 0.0 | 1.2 | 0.9 | 1.4 |
| 34 | Mean Arthritic Score | 7.3 | 0.0* | 4.9 | 4.1 | 7.8 |
|   | SEM | 1.1 | 0.0 | 1.2 | 1.1 | 1.3 |
| 35 | Mean Arthritic Score | 7.5 | 0.0* | 4.9 | 4.0 | 8.0 |
|   | SEM | 1.0 | 0.0 | 1.2 | 1.1 | 1.3 |
| 36 | Mean Arthritic Score | 6.8 | 0.0* | 4.8 | 4.1 | 8.2 |
|   | SEM | 0.9 | 0.0 | 1.1 | 1.1 | 1.1 |
| 37 | Mean Arthritic Score | 7.4 | 0.0* | 4.7 | 4.2 | 8.7 |
|   | SEM | 0.9 | 0.0 | 1.1 | 1.1 | 1.1 |
| 40 | Mean Arthritic Score | 8.2 | 0.0* | 5.0 | 4.7* | 9.0 |
|   | SEM | 0.8 | 0.0 | 1.0 | 1.2 | 0.8 |
| 41 | Mean Arthritic Score | 8.5 | 0.0* | 4.8* | 5.2 | 8.8 |
|   | SEM | 0.7 | 0.0 | 1.0 | 1.1 | 0.8 |

*p < 0.05 significantly different from Vehicle group

Conclusion

Arthritic reactions were noted in all groups from study day 14. Mean total arthritis scores (Table 2) for vehicle treated mice peaked at 8.5±0.72 on study day 41. Mean total arthritis scores in mice treated with hBD2 at 10 mg/kg (Group C) peaked at 5.0±1.04 on study day 40. Mean arthritis scores in this group were lower compared to vehicle treated mice from day 23 until the end of study, however only significantly on study day 41.

Mean total arthritis scores in mice treated with hBD2 at 1 mg/kg (Group D) peaked at 5.2±1.11 on study day 41 and were consistently lower compared to the vehicle treated group from day 21 until the end of study, however only significantly on day 40. Treatment of mice with hBD2 at 0.1 mg/kg (Group E) did not significantly lower mean total arthritis scores compared to the vehicle treated group. The mean score in this group peaked at 9.0±0.77 on study day 40. Mice in the dexamethasone treated group (Group B) displayed a significantly lower arthritic score compared to the vehicle treated group from study day 26 until the end of the study.

To ensure that the removal of mice culled early in the study due to arthritis severity did not artificially skew the data, arthritis scores from such mice were carried over in the analysis until study termination.

Example 2

Anti-Inflammatory Activity of Human Beta Defensin 2 (hBD2)

In human PBMC cultures it was observed that treatment with hBD2 had great influence on the cytokine profile of LPS, LTA or peptidoglycan stimulated cultures. It has previously been observed that hBD2 is able to induce the proinflammatory cytokines and chemokines IL-6, IL-1β, RANTES, IP-10 and IL-8 (Niyonsaba et al. 2007, Boniotto M. et al. 2006).

Here we show that hBD2 has downregulating potential on TNF and IL-1β, two proinflammatory cytokines; and hBD2 also induces IL-10 upon induction of an inflammatory stimulus with lipopolysaccahride (LPS), lipoteichoic acid (LTA) or peptidoglycan (PGN). IL-10 is a potential anti-inflammatory cytokine and hence the resulting effect of hBD2 is anti-inflammatory. This has been observed for human PBMC, a monocytic cell line and a dendritoid cell line.

hBD2 was prepared as described in Example 1.

Isolation and stimulation of PBMC.

Peripheral blood was drawn from healthy volunteers (with approval from the relevant ethical committee in Denmark). Heparinized blood was diluted 1/1 v/v with RPMI and were subjected to Ficoll density centrifugation within 2 h of drawing. Plasma was collected from the top from individual donors and was kept on ice until it was used at 2% in the culture medium (autologous culture medium). Isolated PBMC were resuspended in autologous culture medium and seeded in 96-well culture plates with 255.000 cells per well in a total of 200 µl. PBMC from the same donor were stimulated with 100, 10 or 1 µg/ml of hBD2 either alone or together with LPS at 0.6 ng/ml or 20 ng/ml (E. coli, O111:B4, Sigma L4391), Lipoteichoic acid (LTA) at 1.25 pg/ml (from B. subtilis, Sigma L3265) or peptidoglycan (PGN) at 40 µg/ml (from S. aureus, Sigma 77140). The concentrations used for stimulation were optimized on 3 different donors in initial experiments, for LPS two different concentrations were used to be sure to be on a cytokine level that is possible to modulate. In some experiments PBMC were treated with Dexamethason and Indomethacin alone and together with LPS or LTA as a control on downregulation of inflammatory cytokines. The supernatants were collected after incubation at 37° C. for 24 hours, and stored at −80° C. until cytokine measurement. Viability was measured by Alamar Blue (Biosource, DALL 1100) in all experiments and in some cases also by MTS (Promega) according to manufacturer's instruction and was in some experiments also judged by counting of the cells by a Nucleocounter.

Culture and Stimulation of MUTZ-3

The human myeloid leukaemia-derived cell line MUTZ-3 (DSMZ, Braunschweig, Germany) was maintained in a-MEM (Sigma M4526), supplemented with 20% [volume/volume (v/v)] fetal bovine serum (Sigma F6178) and 40 ng/ml rhGM-CSF (R&D Systems 215-GM-050). These progenitor cells is in the following denoted monocyte cell line and these monocytes were stimulated with 100, 10 or 1 µg/ml of hBD2 either alone or together with LPS or LTA.

Dendritic Cell Differentiation

To generate a dendritoid cell line, the human myeloid leukaemia cell lines MUTZ-3 ($1 \times 10^5$ cells/ml) was differentiated for 7 days in the presence of rhGM-CSF (150 ng/ml) and rhIL-4 (50 ng/ml) into immature DCs. Medium was exchanged every 2-3 days. The differentiated cell line was further stimulated with either LPS or LTA with and without hBD2 to explore the effect of hBD2 on dendritic cells.

Cytokine Measurements.

Cytokine production in supernatants was measured by flow cytometry with a human inflammation cytometric bead array (CBA) according to manufacturer's instructions (BD) on a FACSarray flow cytometer. The following cytokines were measured: IL-8, IL-1β, IL-10, TNF, IL-12 p70, IL-6. In some experiments, cytokines were measured by ELISA kits from R&D systems (IL-10, TNF-α, IL-1β) according to the manufacturer' instruction.

Data Analysis

All experiments were performed at least twice, with representative results shown. The data presented are expressed as mean plus/minus standard deviation (SD). Statistical significance was determined by 2-way ANOVA with the variables being treatment (hBD2, dexamethazone, etc.) and stimulation (LPS, LTA, peptidoglycan, ect.) followed by Bonferroni post-test as reported in the table legends. Differences were considered significant for p<0.05.

Results

The effect of hBD2 was tested on human PBMC treated with and without LPS and LTA (Tables 3, 4 and 5). Treatment with hBD2 gave a significant downregulation of TNF in stimulated cultures for all three tested concentrations (Table 3), the downregulation is dose-dependent for LPS at 0.6 ng/ml and for LTA. For IL-1β the downregualtion was observed mostly at the highest doses (Table 4). Interestingly, IL-10 was significantly and dose-dependently upregulated (Table 5). Downregulation of proinflammatory cytokines and induction of anti-inflammatory cytokines shows a very strong anti-inflammatory potential of hBD2. Viability was measured by two different assays, in order to exclude that the anti-inflammatory effects of hBD2 is due to cytotoxic effects. In Tables 6 and 7 it can be seen that hBD2 have no cytotoxic effect on the cells, the observed effects are stimulatory effects due to stimulation with LPS or LTA that leads to proliferation of the cells. Therefore hBD2 has no cytotoxic effect on these cells.

In Tables 8, 9 and 10, supernatants from another donor were analysed for cytokines by ELISA instead of by a cytometric bead array by flowcytometry and here the same were observed, although the sensitivity of the assay is lower and the detection limit much higher and therefore the effects were not as significant.

In order to test yet another Toll-like receptor ligand, the effect of hBD2 on peptidoglycan stimulated PBMC was investigated (Tables 11 and 12). The same was observed: TNF is dose-dependently downregulated and IL-10 is dose-dependently induced.

As a positive control on downregulation of TNF, two anti-inflammatory compounds, dexamethasone and Indomethacin, were tested in the assay. The concentrations are selected so the compounds are not toxic and achievable concentration due to solubility in medium. Indomethacin only inhibited TNF (Table 13) after stimulation with LTA, whereas dexamethasone effectively downregulated TNF production, the same was observed for IL-1β (Table 15). Indomethacin is a COX-1 and COX-2 inhibitor and is a nonsteroidal anti-inflammatory drug (NSAID) used to treat mild to moderate pain and help relieve symptoms of arthritis and dexamethasone is a synthetic glucocorticoid used primarily in the treatment of inflammatory disorders and it has very potent downregualting effect on proinflammatory cytokines (Rowland et al. 1998) at very low doses, which we also observe for TNF-α and IL-1β. hBD2 is as effective as or better than these two anti-inflammatory compounds.

In Tables 16 and 17, the effect of hBD2 on downregulating TNF in a monocyt cell line and on dendritic cells are shown, the same is observed as was for PBMC. IL-10 was also induced for dendritic cells stimulated with hBD2 and LPS or hBD2 and LTA (results not shown).

In order to exclude that binding of hBD2 to LPS or LTA causes the downregulation of TNF and IL-1β, the effect of hBD2 on stimulation of PBMC with a syntetic ligand (Pam3CSK4 (TLR2-TLR1 ligand), InvivoGen tlrt-pms) was tested. hBD2 was able to downregulate TNF after stimulation with this ligand as well, indicating that neutralization of LPS or LTA is not responsible for the observed effect (results not shown). Moreover, stimulation of dendritic cells with a cytokine cocktail containing TNF-α and IL-α together with hBD2 had downregulating effect on IL-1β and IL-8 and IL-6 compared to stimulation with a cytokine cocktail alone. Obviously no effect on TNF could be analyzed, due to stimulation with TNF-α (results not shown).

TABLE 3

| TNF, pg/ml (SD) | Control | hBD2 100 µg/ml | hBD2 10 µg/ml | hBD2 1 µg/ml |
|---|---|---|---|---|
| Medium | 7.3 (5.9) | 2.9 (5.1) | 2.6 (6.6) | 4.2 (10.7) |
| LPS 0.6 ng/ml | 1708.6 (428.3) | 634.2 (226.1)*** | 1076.4 (278.0)*** | 944.8 (326.6)*** |
| LPS 20 ng/ml | 2572.1 (581.1) | 1733.9 (461.3)*** | 1306.6 (375.0)*** | 1526.9 (444.2)*** |
| LTA 1.25 µg/ml | 1097.4 (293.8) | 375.2 (114.2)*** | 494.7 (158.1)*** | 711.5 (282.5)*** |

TNF production from human peripheral blood mononuclear cells (PBMC) after treatment with LPS or LTA with and without hBD2, all samples tested on the same donor, representative experiment out of 5 donors.
TNF measured by Cytometric Bead Array (CBA) on a FACSarray,
***p < 0.001 compared to respective control (bold), analysed by 2-way ANOVA (N = app. 200 for each data set).

TABLE 4

| IL-1β, pg/ml (SD) | Control | hBD2 100 µg/ml | hBD2 10 µg/ml | hBD2 1 µg/ml |
|---|---|---|---|---|
| Medium | 4.2 (4.7) | 5.3 (7.1) | 3.8 (5.8) | 4.1 (51.0) |
| LPS 0.6 ng/ml | 1734.3 (347.0) | 811.0 (454.4)*** | 1949.8 (396.4)*** | 1436.2 (429.7)*** |
| LPS 20 ng/ml | 2629.5 (533.7) | 1502.1 (407.5)*** | 2273.9 (486.5)*** | 1889.3 (504.8)*** |
| LTA 1.25 µg/ml | 748.5 (172.4) | 538.3 (137.3)*** | 935.3 (238.0)*** | 986.7 (738.7)*** |

IL-1β production from human periferal blood mononuclear cells (PBMC) after treatment with LPS or LTA with and without hBD2, all samples tested on the same donor, representative experiment out of 5 donors.
IL-1β measured by Cytometric bead array (CBA) on a FACSarray,
***p < 0.001 analysed by 2-way ANOVA (N = app. 200 for each data set).

TABLE 5

| IL-10, pg/ml (SD) | Control | hBD2 100 µg/ml | hBD2 10 µg/ml | hBD2 1 µg/ml |
|---|---|---|---|---|
| Medium | 2.09 (8.65) | 2.9 (4.6) | 1.6 (4.1) | 2.09 (4.3) |
| LPS 0.6 ng/ml | 63.15 (302.5) | 232.7 (61.5)*** | 325.7 (88.2)*** | 97.2 (31.1)* |
| LPS 20 ng/ml | 70.4 (22.8) | 383.3 (133.6)*** | 355.8 (99.5)*** | 111.3 (38.8)** |

TABLE 5-continued

| IL-10, pg/ml (SD) | Control | hBD2 100 µg/ml | hBD2 10 µg/ml | hBD2 1 µg/ml |
|---|---|---|---|---|
| LTA 1.25 µg/ml | 14.0 (226.1) | 175.6 (57.0)*** | 136.6 (44.7)*** | 39.9 (16.9) |

IL-10 production from human peripheral blood mononuclear cells (PBMC) after treatment with LPS or LTA with and without hBD2, all samples tested on the same donor, representative experiment out of 5 donors.
IL-10 measured by Cytometric bead array (CBA) on a FACSarray,
*p < 0.001, p < 0.01,
*p < 0.5 analysed by 2-way ANOVA (N = app. 200 for each data set).

TABLE 6

PBMC viability after 24 h of stimulation measured by a MTS assay. Values having a different subscript letter in rows are significantly different tested by 2-way ANOVA followed by Bonferroni post-test.

| Viability, MTS (Abs 490 nm (SD)) | Control | hBD2 100 µg/ml | hBD2 10 µg/ml | hBD2 1 µg/ml |
|---|---|---|---|---|
| Medium | 1.4 (0.2) | 1.2 (0.05)$^a$ | 1.5 (0.2)$^a$ | 1.3 (0.2) |
| LPS 0.6 ng/ml | 1.6 (0.02) | 1.6 (0.1)$^{ab}$ | 2.0 (0.2)$^b$ | 1.5 (0.2) |
| LPS 20 ng/ml | 1.5 (0.1) | 1.9 (0.2)$^b$ | 1.8 (0.3)$^{ab}$ | 1.6 (0.3) |

TABLE 7

| Viability, Alamar Blue (RFU (SD)) | Control | hBD2 100 µg/ml | hBD2 10 µg/ml | hBD2 1 µg/ml |
|---|---|---|---|---|
| Medium | 4097130 (166631) | 3950053 (34466)$^a$ | 3683369 (355296)$^a$ | 4064143 (104634) |
| LPS 0.6 ng/ml | 4279424 (336188) | 4831188 (67646)$^b$ | 4664362 (147776)$^b$ | 4230588 (139745) |
| LPS 20 ng/ml | 4604671 (125840) | 4765256 (41383)$^b$ | 4623818 (56643)$^b$ | 4561739 (138852) |
| LTA 1.25 µg/ml | 4018914 (632833)$^1$ | 4664185 (154023)$^{b,2}$ | 4677870 (10199)$^{b,2}$ | 4148294 (182730)$^{12}$ |

PBMC viability measured by Alamar Blue, one representative experiment out of 5 from 5 different donors. Values having a different superscript letter in rows and values having a different superscript number in columns are significantly different tested by 2-way ANOVA followed by Bonferroni post-test.

TABLE 8

| TNF-α, ng/ml (SD) | Control | hBD2 100 µg/ml | hBD2 10 µg/ml | hBD2 1 µg/ml |
|---|---|---|---|---|
| Medium | nd | nd | nd | nd |
| LPS 0.6 ng/ml | 0.99 (0.27) | 0.41 (0.03)** | 0.59 (0.08)* | 0.70 (0.18) |
| LPS 20 ng/ml | 1.44 (0.31) | 0.53 (0.01)** | 0.49 (0.05)** | 1.18 (0.42) |
| LTA 1.25 µg/ml | 0.90 (0.32) | 0.21 (0.05)* | 0.27 (0.04)* | 0.65 (0.29) |

TNF-alfa secretion from PBMC after stimulation with hBD2, LTA, LPS or combinations hereof. TNF-alfa measured by ELISA,
nd: not detectable, detection limit in assay 0.01 ng/ml,
*p < 0.05 compared to respective control,
**p < 0.01 compared to respective control

TABLE 9

| IL-10, ng/ml (SD) | Control | hBD2 100 µg/ml | hBD2 10 µg/ml | hBD2 1 µg/ml |
|---|---|---|---|---|
| Medium | nd | nd | nd | nd |
| LPS 0.6 ng/ml | nd | 0.14 (0.04) | 0.04 (0.0) | nd |
| LPS 20 ng/ml | nd | 0.46 (0.04) | 0.34 (0.04) | nd |
| LTA 1.25 µg/ml | nd | nd | nd | nd |

IL-10 secretion from PBMC after stimulation with hBD2, LTA, LPS or combinations hereof, TNF-alfa measured by ELISA,
nd: not detectable, detection limit in assay 0.03 ng/ml

TABLE 10

| IL-1β, ng/ml (SD) | Control | hBD2 100 µg/ml | hBD2 10 µg/ml | hBD2 1 µg/ml |
|---|---|---|---|---|
| Medium | nd | nd | nd | nd |
| LPS 0.6 ng/ml | 0.318 (0.087) | 0.275 (0.015) | 0.268 (0.039) | 0.237 (0.007) |
| LPS 20 ng/ml | 0.920 (0.267) | 0.395 (0.033)** | 0.354 (0.013)** | 0.638 (0.159) |
| LTA 1.25 µg/ml | 0.291 (0.092) | 0.281 (0.059) | 0.193 (0.019) | 0.224 (0.030) |

IL-1β secretion from PBMC after stimulation with hBD2, LTA, LPS or combinations hereof, TNF-alfa measured by ELISA,
nd: not detectable, detection limit in assay 0.016 ng/ml,
**$p < 0.01$ compared to respective control

TABLE 11

| TNF, pg/ml (SD) | Control | hBD2 100 µg/ml | hBD2 10 µg/ml | hBD2 1 µg/ml |
|---|---|---|---|---|
| Medium | 0.0 (4.0) | 3.6 (5.3) | 3.7 (6.2) | 3.4 (5.2) |
| PGN 40 µg/ml | 1099.1 (251.6) | 274.9 (71.6)*** | 362.0 (97.7)*** | 809.9 (246.7)*** |

TNF production from human peripheral blood mononuclear cells (PBMC) after treatment with PGN, with and without hBD2; all samples tested on the same donor. TNF measured by Cytometric Bead Array (CBA) on a FACSarray,
***$p < 0.001$ compared to respective control, analysed by 2-way ANOVA (N = app. 200 for each data set).

TABLE 12

| IL-10, pg/ml (SD) | Control | hBD2 100 µg/ml | hBD2 10 µg/ml | hBD2 1 µg/ml |
|---|---|---|---|---|
| Medium | 0.0 (4.1) | 3.0 (9.6) | 3.6 (13.1) | 3.0 (4.8) |
| PGN 40 µg/ml | 381.3 (92.3) | 1054.2 (179.3)*** | 523.4 (111.5)*** | 337.8 (89.1) |

IL-10 production from human peripheral blood mononuclear cells (PBMC) after treatment with PGN, with and without hBD2; all samples tested on the same donor. TNF measured by Cytometric Bead Array (CBA) on a FACSarray,
***$p < 0.001$ compared to respective control, analysed by 2-way ANOVA (N = app. 200 for each data set).

TABLE 13

| TNF, ng/ml (SD) | Medium | LPS 0.6 ng/ml | LPS 20 ng/ml | LTA 1.25 µg/ml |
|---|---|---|---|---|
| Control | 0.0 (0.0) | 1.43 (0.05) | 2.84 (0.07) | 6.72 (0.14) |
| Dexamethason 35 ng/ml | 0.0 (0.0) | <u>0.038</u> (0.004) | <u>1.69</u> (0.05) | <u>1.75</u> (0.05) |
| Dexamethason 3.5 ng/ml | 0.0 (0.0) | <u>0.30</u> (0.01) | <u>0.91</u> (0.03) | <u>2.05</u> (0.06) |
| Dexamethason 0.35 ng/ml | 0.0 (0.0) | <u>0.61</u> (0.02) | 6.04 (0.14) | <u>4.73</u> (0.10) |
| Indomethacin 7.2 ug/ml | 0.0 (0.0) | 1.71 (0.07) | 2.70 (0.07) | <u>5.80</u> (0.13) |
| Indomethacin 0.72 ug/ml | 0.0 (0.0) | 1.56 (0.04) | 7.54 (0.17) | <u>5.50</u> (0.13) |
| hBD2 1000 µg/ml | 0.0 (0.0) | <u>0.003</u> (0.002) | <u>0.000</u> (0.002) | <u>0.11</u> (0.01) |
| hBD2 100 µg/ml | 0.0 (0.0) | <u>0.000</u> (0.002) | <u>0.038</u> (0.003) | <u>1.15</u> (0.04) |
| hBD2 10 µg/ml | 0.0 (0.0) | <u>0.20</u> (0.01) | <u>0.35</u> (0.01) | <u>2.33</u> (0.06) |
| hBD2 1 µg/ml | 0.0 (0.0) | <u>0.17</u> (0.01) | 6.24 (0.14) | <u>3.90</u> (0.10) |

TNF production from human peripheral blood mononuclear cells (PBMC) after treatment with LPS or LTA, with and without hBD2 or two different controls for inhibition of TNF (Dexamethasone and Indomethacin); all samples tested on the same donor. TNF measured by Cytometric Bead Array (CBA) on a FACSarray, values underlined are significantly reduced compared to respective control (bold), analysed by 2-way ANOVA (N = app. 200 for each data set).

TABLE 14

| IL-10, pg/ml (SD) | Medium | LPS 0.6 ng/ml | LPS 20 ng/ml | LTA 1.25 µg/ml |
|---|---|---|---|---|
| Control | 0.0 (218.8) | 53.9 (3.1) | 123.4 (4.6) | 170.1 (5.5) |
| Dexamethason 35 ng/ml | 0.0 (1.4) | <u>100.4</u> (3.8) | <u>152.5</u> (5.2) | 175.2 (6.6) |
| Dexamethason 3.5 ng/ml | 2.7 (1.9) | 64.6 (3.3) | 122.8 (4.7) | 112.5 (3.9) |
| Dexamethason 0.35 ng/ml | 3.9 (1.9) | 46.8 (2.8) | 197.1 (7.2) | 126.6 (4.7) |
| Indomethacin 7.2 ug/ml | 0.0 (1.5) | 45.7 (2.5) | 77.9 (3.6) | 90.4 (4.9) |
| Indomethacin 0.72 ug/ml | 0.0 (1.4) | 37.3 (19.6) | 108.0 (4.4) | 84.9 (3.5) |
| hBD2 1000 µg/ml | 0.0 (1.6) | 30.8 (2.6) | 50.5 (3.2) | <u>465.2</u> (16.3) |
| hBD2 100 µg/ml | 0.0 (4.9) | <u>173.5</u> (5.7) | <u>885.2</u> (22.2) | <u>766.0</u> (21.7) |
| hBD2 10 µg/ml | 3.9 (1.7) | <u>165.1</u> (5.6) | <u>497.5</u> (13.5) | <u>355.8</u> (9.4) |
| hBD2 1 µg/ml | 0.0 (1.9) | 42.7 (2.8) | <u>207.0</u> (6.9) | 142.1 (4.9) |

IL-10 production from human peripheral blood mononuclear cells (PBMC) after treatment with LPS or LTA, with and without hBD2 or two different controls for antiinflammatory effects (Dexamethasone and Indomethacin); all samples tested on the same donor. IL-10 measured by Cytometric Bead Array (CBA) on a FACSarray, values underlined are significantly increased compared to respective control (bold), analysed by 2-way ANOVA (N = app. 200 for each data set).

TABLE 15

| IL-1β, ng/ml (SD) | Medium | LPS 0.6 ng/ml | LPS 20 ng/ml | LTA 1.25 µg/ml |
|---|---|---|---|---|
| Control | 0.00 (0.06) | 3.96 (0.18) | 6.58 (0.23) | 11.47 (0.38) |
| Dexamethason 35 ng/ml | 0.00 (0.00) | <u>1.00</u> (0.03) | <u>2.32</u> (0.07) | <u>3.98</u> (0.14) |
| Dexamethason 3.5 ng/ml | 0.00 (0.00) | <u>1.90</u> (0.06) | <u>3.58</u> (0.12) | <u>5.22</u> (0.19) |
| Dexamethason 0.35 ng/ml | 0.01 (0.00) | <u>2.9</u> (0.09) | <u>5.56</u> (0.18) | <u>7.91</u> (0.28) |
| Indomethacin 7.2 ug/ml | 0.04 (0.00) | 4.1 (0.13) | 6.12 (0.23) | <u>8.91</u> (0.30) |
| Indomethacin 0.72 ug/ml | 0.01 (0.00) | 3.1 (0.18) | 6.46 (0.22) | <u>7.53</u> (0.31) |
| hBD2 1000 µg/ml | 0.01 (0.00) | <u>0.53</u> (0.02) | <u>1.19</u> (0.08) | <u>4.43</u> (0.14) |
| hBD2 100 µg/ml | 0.00 (0.00) | <u>0.38</u> (0.01) | <u>1.67</u> (0.05) | <u>9.12</u> (0.32) |
| hBD2 10 µg/ml | 0.06 (0.00) | <u>1.13</u> (0.04) | <u>3.58</u> (0.12) | <u>11.0</u> (0.37) |

TABLE 15-continued

| IL-1β, ng/ml (SD) | Medium | LPS 0.6 ng/ml | LPS 20 ng/ml | LTA 1.25 µg/ml |
|---|---|---|---|---|
| hBD2 1 µg/ml | 0.01 (0.00) | <u>1.83</u> (0.06) | <u>4.91</u> (0.19) | <u>8.87</u> (0.29) |

IL-1β production from human peripheral blood mononuclear cells (PBMC) after treatment with LPS or LTA, with and without hBD2 or two different controls for antiinflammatory effects (Dexamethasone and Indomethacin); all samples tested on the same donor. IL-1β measured by Cytometric Bead Array (CBA) on a FACSarray, values underlined are significantly reduced compared to respective control (bold), analysed by 2-way ANOVA (N = app. 200 for each data set).

TABLE 16

| TNF, pg/ml (SD) | Control | hBD2 100 µg/ml | hBD2 10 µg/ml | hBD2 1 µg/ml |
|---|---|---|---|---|
| Medium | 0.00 (5.56) | 0.00 (5.47) | 2.60 (7.17) | 2.21 (7.88) |
| LPS 1.5 µg/ml | 6.38 (9.28) | 3.93 (6.63)* | 3.93 (6.93)* | 6.61 (9.17) |
| LTA 1.5 µg/ml | 5.28 (9.75) | 2.64 (29.19)* | 3.76 (7.72) | 1.75 (6.96)** |

TNF production in supernatant from a human monocyte cell line (MUTZ-3) after treatment with LPS or LTA, with and without hBD2. TNF measured by Cytometric Bead Array (CBA) on a FACSarray,
*p < 0.05 compared to respective control,
**p < 0.01 compared to respective control, analysed by 2-way ANOVA (N = app. 200 for each data set).

TABLE 17

| TNF, pg/ml (SD) | Control | hBD2 100 µg/ml | hBD2 10 µg/ml | hBD2 1 µg/ml |
|---|---|---|---|---|
| Medium | 0.00 (1.74) | 0.00 (1.83) | 1.89 (2.15) | 4.64 (10.26) |
| LPS 1.5 µg/ml | 23.73 (3.28) | 7.66 (2.51)*** | 13.8 (2.33)*** | 18.04 (2.89)*** |
| LTA 1.5 µg/ml | 3.78 (2.26) | 5.22 (2.25) | 2.76 (2.27)* | 0.00 (1.98)*** |

TNF production in supernatants from immature dendritic cells stimulated with LPS or LTA (to generate mature DC), with and without hBD2. TNF measured by Cytometric Bead Array (CBA) on a FACSarray, *significantly reduced p < 0.05 compared to respective control, ***significantly reduced p < 0.01 compared to respective control, analysed by 2-way ANOVA (N = app. 200 for each data set).

Example 3

Anti-Inflammatory Activity of hBD1, hBD2, hBD3, and a hBD4 Variant

Example 3 was carried out essentially as described in Example 2. The compound rhBD2, as shown in the tables below, is recombinant hBD2, which is identical to hBD2 as used in Example 2.

The compounds hBD1, hBD2, hBD3 and hBD4 variant, as shown in the tables below, were prepared using chemical synthesis, and obtained from Peptide Institute Inc.

The amino acid sequence of recombinant hBD2 (rhBD2) is identical to the amino acid sequence of hBD2 prepared by chemical synthesis.

The hBD4 variant shown in the tables below consists of amino acids 3-39 of hBD4, and the amino acid sequence is shown as SEQ ID NO:5.

In each table, all samples were tested on the same donor. SD means standard deviation.

Results

TABLE 18

| Test compound | Medium TNF pg/ml (SD) | Medium % of control | LPS 20 ng/ml TNF pg/ml (SD) | LPS 20 ng/ml % of control | LPS 0.6 ng/ml TNF pg/ml (SD) | LPS 0.6 ng/ml % of control |
|---|---|---|---|---|---|---|
| Medium (non-treated) | 1 (1) | 100% | 2164 (632) | 100% | 728 (156) | 100% |
| rhBD2 40 µg/ml | 0 (0) | — | 167 (17)*** | 8% | 74 (5)*** | 10% |
| rhBD2 10 µg/ml | 0 (0) | — | 260 (29)*** | 12% | 125 (20)** | 17% |
| rhBD2 1 µg/ml | 1 (0) | — | 918 (373)*** | 42% | 196 (104)** | 27% |
| hBD1 40 µg/ml | 0 (0) | — | 999 (116)*** | 46% | 91 (8)** | 13% |
| hBD1 10 µg/ml | 0 (1) | — | 1311 (417)*** | 61% | 203 (20)** | 28% |
| hBD1 1 µg/ml | 1 (1) | — | 1395 (201)*** | 64% | 474 (187) | 65% |
| hBD2 40 µg/ml | 0 (0) | — | 52 (71)*** | 2% | 176 (103)** | 24% |
| hBD2 10 µg/ml | 0 (0) | — | 132 (179)*** | 6% | 304 (108)* | 42% |
| hBD2 1 µg/ml | 0 (0) | — | 411 (581)*** | 19% | 242 (30)* | 33% |
| HBD-3 1 µg/ml | 0 (0) | — | 451 (24)*** | 21% | 528 (98) | 73% |
| hBD4 variant 10 µg/ml | 0 (0) | — | 139 (6)*** | 6% | 211 (22)** | 29% |
| hBD4 variant 1 µg/ml | 0 (0) | — | 778 (27)*** | 36% | 468 (59) | 64% |
| Dexamethasone | 0 (0) | — | 635 (163)*** | 29% | 47 (8)*** | 6% |

TABLE 18-continued

|  | Medium | | LPS 20 ng/ml | | LPS 0.6 ng/ml | |
| --- | --- | --- | --- | --- | --- | --- |
| Test compound | TNF pg/ml (SD) | % of control | TNF pg/ml (SD) | % of control | TNF pg/ml (SD) | % of control |
| Infliximab | 0 (0) | — | 0 (0)*** | 0% | 0 (0)*** | 0% |

TNF production from human peripheral blood mononuclear cells (PBMC) after treatment with LPS with and without human beta defensins, dexamethasone or Infliximab. TNF measured by Cytometric Bead Array (CBA) on a FACSarray,
*$p < 0.05$,
**$p < 0.01$,
***$p < 0.001$ analyzed by 2-way ANOVA and compared to non-treated cells by Bonferroni posttests.

TABLE 19

|  | Medium | | LPS 20 ng/ml | | LPS 0.6 ng/ml | |
| --- | --- | --- | --- | --- | --- | --- |
| Test compound | IL-10 pg/ml (SD) | % of control | IL-10 pg/ml (SD) | % of control | IL-10 pg/ml (SD) | % of control |
| Medium (non-treated) | 0 (0) | 100% | 111 (3) | 100% | 66 (5) | 100% |
| rhBD2 40 µg/ml | 0 (0) | — | 281 (9)*** | 252% | 108 (4)* | 162% |
| rhBD2 10 µg/ml | 0 (0) | — | 243 (38)*** | 218% | 103 (14)* | 155% |
| rhBD2 1 µg/ml | 0 (0) | — | 126 (14) | 113% | 72 (9) | 108% |
| hBD1 40 µg/ml | 0 (0) | — | 113 (5) | 102% | 69 (4) | 104% |
| hBD1 10 µg/ml | 0 (0) | — | 100 (1) | 90% | 76 (13) | 114% |
| hBD1 1 µg/ml | 0 (0) | — | 95 (17) | 85% | 71 (6) | 108% |
| hBD2 40 µg/ml | 0 (0) | — | 323 (0)*** | 290% | 131 (13)*** | 197% |
| hBD2 10 µg/ml | 0 (0) | — | 240 (0)*** | 215% | 86 (6) | 130% |
| hBD2 1 µg/ml | 0 (0) | — | 123 (0) | 110% | 53 (5) | 80% |
| hBD3 1 µg/ml | 0 (0) | — | 152 (72)* | 137% | 71 (2) | 107% |
| hBD4 variant 10 µg/ml | 0 (0) | — | 187 (9)*** | 168% | 92 (17) | 139% |
| hBD4 variant 1 µg/ml | 0 (0) | — | 175 (8)*** | 157% | 90 (14) | 136% |
| Dexamethasone | 0 (0) | — | 75 (6)* | 67% | 47 (3) | 70% |
| Infliximab | 0 (0) | — | 63 (7)** | 56% | 46 (9) | 69% |

IL-10 production from human peripheral blood mononuclear cells (PBMC) after treatment with LPS with and without human beta defensins, dexamethasone or Infliximab. IL-10 measured by Cytometric Bead Array (CBA) on a FACSarray,
*$p < 0.05$,
**$p < 0.01$,
***$p < 0.001$ analyzed by 2-way ANOVA and compared to non-treated cells by Bonferroni posttests.

TABLE 20

|  | Medium | | LPS 20 ng/ml | | LPS 0.6 ng/ml | |
| --- | --- | --- | --- | --- | --- | --- |
| Test compound | IL-1β pg/ml (SD) | % of control | IL-1β pg/ml (SD) | % of control | IL-1β pg/ml (SD) | % of control |
| Medium (non-treated) | 0 (0) | 100% | 2544 (226) | 100% | 741 (93) | 100% |
| rhBD2 40 µg/ml | 0 (0) | — | 395 (25)*** | 16% | 124 (11)*** | 17% |
| rhBD2 10 µg/ml | 0 (0) | — | 624 (37)*** | 25% | 214 (7)*** | 29% |

TABLE 20-continued

| Test compound | Medium IL-1β pg/ml (SD) | % of control | LPS 20 ng/ml IL-1β pg/ml (SD) | % of control | LPS 0.6 ng/ml IL-1β pg/ml (SD) | % of control |
|---|---|---|---|---|---|---|
| rhBD2 1 µg/ml | 0 (0) | — | 1480 (154)*** | 58% | 284 (15)*** | 38% |
| hBD1 40 µg/ml | 0 (0) | — | 1599 (14)*** | 63% | 302 (3)*** | 41% |
| hBD1 10 µg/ml | 0 (0) | — | 1913 (53)*** | 75% | 401 (17)*** | 54% |
| hBD1 1 µg/ml | 0 (0) | — | 2087 (157)*** | 82% | 512 (45)** | 69% |
| hBD2 40 µg/ml | 1 (1) | — | 316 (0)*** | 12% | 159 (2)*** | 21% |
| hBD2 10 µg/ml | 0 (0) | — | 589 (0)*** | 23% | 238 (124)*** | 32% |
| hBD2 1 µg/ml | 0 (0) | — | 1569 (0)*** | 62% | 312 (28)*** | 42% |
| hBD3 1 µg/ml | 0 (0) | — | 568 (126)*** | 22% | 331 (23)*** | 45% |
| hBD4 variant 10 µg/ml | 0 (0) | — | 463 (40)*** | 18% | 163 (5)*** | 22% |
| hBD4 variant 1 µg/ml | 0 (0) | — | 1004 (24)*** | 40% | 286 (11)*** | 39% |
| Dexamethasone | 0 (0) | — | 1120 (220)*** | 44% | 104 (8)*** | 14% |
| Infliximab | 0 (0) | — | 2704 (0) | 106% | 636 (81) | 86% |

IL-1β production from human peripheral blood mononuclear cells (PBMC) after treatment with LPS with and without human beta defensins, dexamethasone or Infliximab. IL-1β measured by Cytometric Bead Array (CBA) on a FACSarray, ***p < 0.001 analyzed by 2-way ANOVA and compared to non-treated cells by Bonferroni posttests.

The effects of hBD1, hBD2, hBD3 and a hBD4 variant were tested on human PBMC treated with and without LPS (Tables 18, 19 and 20). For comparison, rhBD2 was included in each setup.

TNF was downregulated for all defensins. The reduction in IL-1β secretion was comparable to TNF, although not as pronounced as TNF. Secretion of IL-10 was significantly and dose-dependently enhanced for hBD2 and the hBD4 variant.

hBD3 was also tested at 10 µg/ml and 40 µg/ml and the hBD4 variant was also tested at 40 µg/ml; however, since both molecules were toxic to the cells at the these concentrations, it was not possible to discriminate between toxic and anti-inflammatory effects.

As a positive control on downregulation of TNF, two anti-inflammatory compounds, Dexamethasone and Infliximab, were included in the setup.
Conclusion All the tested human beta defensins showed anti-inflammatory potential.

Example 4

Reduction of IL-23 from Human Monocyte-Derived Dendritic Cells and Human PBMCs

Example 4 was carried out essentially as described in Example 2 for human PBMCs; however, the readout was IL-23 instead of TNF, IL-1β and IL-10. Moreover, the effect of rhBD2 on human monocyte-derived dendritic cells was also investigated.
Generation of Monocyte-Derived Dendritic Cells (DCs)

The DCs were prepared according to a modified protocol originally described by Romani et al. Briefly, peripheral blood mononuclear cells (PBMCs) were purified from buffy coats of healthy donors by centrifugation over a Ficoll-pague (GE-healthcare) gradient. Monocytes were isolated from PBMC by positive selection of CD14+ cells by magnetic beads (Dynal, Invitrogen) according to the manufacturer's instructions. The CD14+ monocytes were cultured in 6-well plates in RPMI/2% Human AB Serum recombinant human recombinant granulocyte-marcrophage colony-stimulating factor (GM-CSF, 20 ng/ml) and IL-4 (20 ng/ml)(PeproTech) for 6 days, replenishing the medium/cytokines after 2 and 5 days. After 6 days of culture the immature DCs are re-cultured into 96-well plates in a concentration of $1 \times 10^6$ cells/ml and left untreated or treated with a cocktail and/or hBD2 for a further 24 h. hBD2 was tested in four concentrations in quadruplicate. hBD2 was analyzed for its ability to suppress hDC-maturation into a proinflammatory phenotype using a proinflammatory cocktail that contained LPS (100 ng/ml) and IFN-γ (20 ng/ml). Dexamethasone was added 20 h prior to the cocktail as positive control for a compound with proven clinical anti-inflammatory activity. The incubation with hBD2 was done 4 h prior to addition of cocktail.
Cytokine ELISA Cell culture supernatants were collected and stored at −80° C. Amounts of IL-23 was measured by standard sandwich ELISA using commercially available antibodies and standards according to the manufacturer's protocols (eBioscience).
MTT Assay A MTT based cell growth determination kit was used as a measure of cell survival after 48 h in order to evaluate if any of the cells were severely affected by treatment with vehicles, cocktail or hBD2 and was done according to the manufacturer's protocols (Sigma).
Statistical Analyses All experiments were performed at least twice, with representative results shown. The data presented are expressed as mean plus/minus standard deviation (SEM). Statistical significance was determined by 2-way ANOVA with the variables being treatment (hBD2, dexamethazone, ect.) and stimulation (LPS, LTA, peptidoglycan, ect.) followed by Bonferroni post-test as reported in the table legends. Differences were considered significant for p<0.05.
Results

TABLE 21

| IL-23 pg/ml (SEM) | Unstimulated | LPS (100 ng/ml) and IFN-γ (20 ng/ml) |
|---|---|---|
| Untreated | 375 (96) | 3569 (130) |
| hBD2 1 µg/ml | nd | 3833 (88) |
| hBD2 10 µg/ml | 451 (121) | 3308 (169)* |
| hBD2 30 µg/ml | nd | 3042 (46)*** |
| hBD2 100 µg/ml | nd | 2145 (202)*** |
| Dexamethasone 1 µM | 424 (38) | 1147 (268)*** |

IL-23 (pg/ml) in supernatants of human CD14+ monocyte-derived dendritic cells stimulated with either medium (unstimulated), or LPS and IFN-γ and treated with either medium (untreated), hBD2 or Dexamehtasone, average (SEM), N = 4, one representative donor out of three.
*p < 0.05,
**p < 0.01,
***p < 0.001 analyzed by 2-way ANOVA and compared to non-treated cells by Bonferroni posttests. nd: not detected (below detection limit).

TABLE 22

| IL-23 pg/ml (SEM) | Control | LPS 0.6 ng/ml | LPS 20 ng/ml | LTA 5 µg/ml |
|---|---|---|---|---|
| Control (non-treated) | 257 (7) | 553 (6) | 510 (5) | 762 (20) |
| hBD2 1 µg/ml | 218 (5) | 338 (10)** | 263 (5)** | 383 (20)** |
| hBD2 10 µg/ml | 211 (4) | 462 (2)* | 295 (1)** | 438 (9)** |
| hBD2 100 µg/ml | 207 (4) | 484 (7) | 488 (8) | 810 (30) |
| Dexamethasone 3.5 ng/ml | 222 (5) | 202 (5)** | 192 (1)** | 223 (1)** |
| Infliximab 1 µg/ml | 227 (10) | 356 (10)** | 373 (2)** | 349 (1)** |

IL-23 (pg/ml) in supernatants of human PBMC stimulated with either medium (control), 0.6 ng/ml LPS, 20 ng/ml LPS or 5 µg/ml LTA and treated hBD2, Dexamethasone or Infliximab, average (SEM).
*p < 0.05, **p < 0.01,
***p < 0.001 analyzed by 1-way ANOVA and compared to non-treated cells by Dunnett's Multiple Comparison posttest.

As shown in Table 21, hBD2 suppresses significantly and dose-dependently IL-23 secretion from human CD14+ monocyte-derived dendritic cells.

For human PBMC, IL-23 secretion was also significantly suppressed (Table 22). On these cells there was an inverse dose-dependency, that was found to be a bell-shaped dose-response inhibition curve when testing lower doses of hBD2 (data not shown).

This shows that hBD2 might have a suppressive effect in a cronic autoimmune condition by suppression of IL-23 secretion, as IL-23 is an important part of the inflammatory response. Th17 cells are dependent on L-23 for their survival and expansion and Th17 cells have been shown to be pathogenic in several autoimmune diseases, such as Crohn's disease, ulcerative colitis, psoriasis and multiple sclerosis.

Example 5

Reduction of TNF Secretion from PBMCs with Mouse Beta Defensin 3 (mBD3)

Example 5 was carried out essentially as described in Example 2 for human PBMCs. Mouse beta defensin 3 (mBD3) was prepared using the same protocol as was used for production of hBD2 in Example 1. The amino acid sequence of mBD3 is shown in SEQ ID NO:6. Mouse PBMCs were prepared as described below.

Isolation and Stimulation of Mouse Peripheral Blood Mononuclear Cells (PBMC)

Mouse peripheral blood mononuclear cells were isolated from blood of ten NMRI mice. In short, heparinized blood was diluted 1/1 v/v with RPMI and subjected to Ficoll density centrifugation within 2 h of drawing. Plasma was collected from the top and discarded. Isolated PBMC were resuspended in culture medium (RPMI 1640 (Gibco, 42401) w/1% penicillin and streptomycin and 1% L-Glutamine) and seeded in 96-well culture plates with 115.500 cells per well in a total of 200 µl. PBMC from the same donor were stimulated with 100, 10 or 1 µg/ml of hBD2 or mBD3 (mouse beta defensin 3); either alone or together with 20 ng/ml LPS (*E. coli*, O111:B4, Sigma L4391). Dexamethasone was added at 3.5 ng/ml to cultures with and without LPS stimulation. The supernatants were collected after incubation at 37° C. for 24 hours, and stored at −80° C. until cytokine measurement.

Cytokine production in supernatants was measured by flow cytometry with a mouse inflammation cytometric bead array (CBA) according to manufacturer's instructions (BD) on a FACSarray flow cytometer.

Viability was measured by Alamar Blue (Biosource DALL 1100) after supernatant were collected.
Results

TABLE 23

| TNF pg/ml (SEM) | Medium | LPS 20 ng/ml |
|---|---|---|
| Medium | 5 (1) | 1353 (140) |
| mBD3 1 µg/ml | 2 (0) | 384 (11)*** |
| mBD3 10 µg/ml | 2 (0) | 51 (1)*** |
| mBD3 100 µg/ml | 39 (19) | 166 (17)*** |
| hBD2 1 µg/ml | 3 (0) | 633 (110)*** |
| hBD2 10 µg/ml | 2 (0) | 359 (10)*** |
| hBD2 100 µg/ml | 2 (0) | 342 (34)*** |
| Dexamethasone 3.5 ng/ml | 1 (0) | 460 (29)*** |
| Infliximab 1 µg/ml | 0 (0) | 1 (0)*** |

TNF production from human peripheral blood mononuclear cells (PBMC) after treatment with LPS with and without hBD2, all samples tested on the same donor, representative experiment out of two donors. TNF measured by Cytometric Bead Array (CBA) on a FACSarray,
***p < 0.001 compared to respective control, analysed by 2-way ANOVA (N = 2).

TABLE 24

| TNF pg/ml (SEM) | Medium | LPS 20 ng/ml |
|---|---|---|
| Medium | 578 (3) | 2063 (77) |
| mBD3 1 µg/ml | 347 (32) | 1600 (47)*** |
| mBD3 10 µg/ml | 180 (0) | 297 (9)*** |
| mBD3 100 µg/ml | 182 (5) | 195 (6)*** |

TABLE 24-continued

| TNF pg/ml (SEM) | Medium | LPS 20 ng/ml |
|---|---|---|
| Dexamethasone 3.5 ng/ml | 94 (3) | 328 (8)*** |
| Infliximab 1 µg/ml | 530 (4) | 2119 (31) |

TNF production from mouse peripheral blood mononuclear cells (PBMC) after treatment with LPS with and without mBD3, all samples tested on the same donor, representative experiment out of two donors. TNF measured by Cytometric Bead Array (CBA) on a FACSarray.
***$p < 0.001$ compared to respective control, analysed by 2-way ANOVA (N = 2).

As shown in Table 23, mouse beta defensin 3 (mBD3) is downregulating the secretion of TNF from human PBMCs to the same extend as hBD2 and dexamethason. mBD3 also downregulate the secretion of TNF from mouse PBMC (Table 24).

Accordingly, in this setup, mBD3 exhibits excellent anti-inflammatory activity.

References

Bonoiotto M., W J Jordan, J. Eskdale, A. Tossi, N. Antcheva, S. Crovella, ND Connell and G Gallagher. Human β-Defensin 2 Induces a Vigorous Cytokine Response in Peripheral Blood Mononuclear Cells. *Antimicrobial Agents and Chemotherapy* (2006), 50, 1433-1441.

Bowdish et al., Immunomodulatory properties of defensins and cathelicidins. *Curr. Top. Microbiol. Immunol.* (2006) 306, 27-66.

Gersemann et al., Crohn's disease-defect in innate defence. *World J. Gastroenterol.* (2008) 14, 5499-5503.

Lehrer R. I., Primate defensins. *Nat. Rev. Microbiol.* (2004) 2, 727-738.

Swidsinski et al., Mucosal flora in inflammatory bowel disease. *Gastroenterology* (2002) 122, 44-54.

Niyonsaba F., H. Ushio, N. Nakano, W. Ng, K. Sayama, K. Hashimoto, I. Nagaoka, K. Okumura and H. Ogawa. Antimicrobial peptides human β-defensins stimulate epidermal keratinocyte migration, proliferation and production of proinflammatory cytokines and chemokines. *Journal of Investigative Dermatology* (2007), 127, 594-604.

Rowland T L, S M McHugh, J Deighton, R J Dearman, P W Ewan and I Kimber. Differential regulation by thalidomide and dexamethasone of cytokine expression in human peripheral blood mononuclear cells. *Immunopharmacology* (1998), 40, 11-20.

Wang et al., Host-microbe interaction: mechanisms of defensin deficiency in Crohn's disease. *Expert. Rev. Anti. Infect. Ther.* (2007) 5, 1049-1057.

Wehkamp et al., Reduced Paneth cell alpha-defensins in ileal Crohn's disease. *Proc. Natl. Acad. Sci. U.S.A* (2005) 102, 18129-18134.

---

The invention claimed is:

1. A method of treating rheumatoid arthritis, comprising administering to a subject in need of such treatment an effective amount of a beta-defensin comprising an amino acid sequence that has at least 95% identity to the amino acid sequence of SEQ ID NO:2.

2. The method of claim 1, wherein the beta-defensin is administered parenterally.

3. The method of claim 1, wherein the beta-defensin is administered subcutaneously or intravenously.

4. The method of claim 1, wherein the beta-defensin is administered at a dosage of from about 0.1 to about 100 mg/kg body weight per day.

5. The method of claim 1, wherein the beta-defensin is administered at a dosage of from about 0.1 to about 10 mg/kg body weight per day.

6. The method of claim 1, wherein the beta-defensin comprises the amino acid sequence of SEQ ID NO:2.

7. The method of claim 1, wherein the beta-defensin consists of the amino acid sequence of SEQ ID NO:2.

8. The method of claim 1, wherein the beta defensin comprises conserved cysteine residues corresponding to amino acid positions 8, 15, 20, 30, 37, 38 of SEQ ID NO: 2.

9. The method of claim 1, wherein any amino acid substitution in the beta defensin relative to SEQ ID NO: 2 is a conservative substitution.

* * * * *